US011951239B2

(12) United States Patent
Luo

(10) Patent No.: US 11,951,239 B2
(45) Date of Patent: Apr. 9, 2024

(54) DETACHABLE BREAST PUMP

(71) Applicant: Guangzhou Talong Technology Co., Ltd., Guangzhou (CN)

(72) Inventor: Likang Luo, Guangzhou (CN)

(73) Assignee: GUANGZHOU TALONG TECHNOLOGY CO., LTD., Guangzhou (CN)

( * ) Notice: Subject to any disclaimer, the term of this patent is extended or adjusted under 35 U.S.C. 154(b) by 0 days.

(21) Appl. No.: 18/359,110

(22) Filed: Jul. 26, 2023

(65) Prior Publication Data

US 2023/0364310 A1 Nov. 16, 2023

(30) Foreign Application Priority Data

Jun. 6, 2023 (CN) .......................... 202321436089.7

(51) Int. Cl.
*A61M 1/06* (2006.01)
*A61M 1/00* (2006.01)

(52) U.S. Cl.
CPC ............... *A61M 1/06* (2013.01); *A61M 1/067* (2021.05); *A61M 1/65* (2021.05)

(58) Field of Classification Search
CPC ........ A61M 1/06; A61M 1/067; A61M 1/069; A61M 1/0697; A61M 1/0693; A61M 1/64; A61M 1/65
See application file for complete search history.

(56) References Cited

U.S. PATENT DOCUMENTS

| 2005/0256449 | A1  | 11/2005 | Tashiro |
| 2008/0275386 | A1* | 11/2008 | Myers ..................... A61M 1/81 604/74 |
| 2014/0052057 | A1  | 2/2014  | Darnell et al. |
| 2017/0182231 | A1  | 6/2017  | Aalders et al. |

* cited by examiner

*Primary Examiner* — Robert J Utama
*Assistant Examiner* — Justin L Zamory
(74) *Attorney, Agent, or Firm* — Zhigang Ma

(57) ABSTRACT

The present disclosure provides a detachable breast pump, including a host machine, a cup and a flowing channel unit. The host machine includes a variable pressure chamber. The cup is detachably connected to the host machine through the variable pressure chamber, and the variable pressure chamber is provided thereon with a pressure transmission channel extended to an inside of the host machine. The flowing channel unit is detachably arranged inside the cup and separates an internal space of the cup into a flowing channel and a milk storage bowl. The flowing channel is communicated with the variable pressure chamber, the milk storage bowl and the outside. With the detachable breast pump, the host machine is detachably connected to the cup, facilitating convenient demounting and cleaning, reducing the labor of reinstalling after demounting and cleaning, and improving the convenience of usage.

6 Claims, 6 Drawing Sheets

DETACHABLE BREAST PUMP

TECHNICAL FIELD

The present disclosure belongs to the technical field of breast milking equipment, more particularly to a detachable breast pump.

BACKGROUND

Breast pump refers to a tool used for squeezing out the milk accumulated in the breast, which is generally employed when an infant cannot directly suck on the breast, or when the mother's nipples are experiencing a problem, or when a working mother still hopes to breastfeed an infant.

Current breast pumps include a host machine, a milking structure and a milk bottle, which are independent of each other. During practical application, the milk might infiltrate into the host machine while the milking structure is working, whereby impacting each electronic component inside the host machine and finally resulting in abnormal operation of the host machine.

SUMMARY

It is an object of the present disclosure to provide a detachable breast pump, to address the above problems in the existing technologies.

In order to achieve the above purpose, the present disclosure employs the following technical solution.

A detachable breast pump includes a host machine, a cup and a flowing channel unit.

The host machine includes a variable pressure chamber. The cup is detachably connected to the host machine through the variable pressure chamber, and the variable pressure chamber is provided thereon with a pressure transmission channel extended to an inside of the host machine.

The flowing channel unit is detachably arranged inside the cup and separates an internal space of the cup into a flowing channel and a milk storage bowl. The flowing channel is communicated with the variable pressure chamber, the milk storage bowl and the outside.

In one possible design, the host machine includes a housing, a control module and an air pump module. The housing is provided with a partition plate at one end and is connected to the variable pressure chamber through the partition plate. The partition plate is provided thereon with a first pipe configured to communicate with the variable pressure chamber.

The control module and the air pump module are both arranged inside the housing. The control module is connected to the air pump module in a communication manner. The air pump module is connected to the variable pressure chamber through the first pipe.

In one possible design, the variable pressure chamber includes a spacer and a silicone suction cup.

The spacer is detachably connected to the partition plate and is provided thereon with a second pipe.

The silicone suction cup includes an annular connection part and a suction cup body. The annular connection part has an upper end connected to the spacer and a lower end integrated with the suction cup body. The suction cup body is arranged opposite to the spacer to enclose a variable pressure chamber body.

Correspondingly, the second pipe has an upper end communicated with the first pipe and a lower end communicated with the variable pressure chamber body. The first pipe and the second pipe constitute the pressure transmission channel.

In one possible design, the spacer includes a spacer body and a peripheral connection part. The spacer body is arranged opposite to the partition plate. An outer circumference of the spacer body is connected to the peripheral connection part. The peripheral connection part includes an inner annular surface and a clamping groove with a downward opening. The inner annular surface is clamped to the partition plate through a snap ring. The clamping groove is configured to connect to the annular connection part. Correspondingly, the partition plate has a bottom surface provided thereon with an annular plate fitting with the inner annular surface.

In one possible design, the air pump module includes an air pump, a valve body and an air pipe. The air pump and the valve body are each connected to the control module in a communication manner. The air pipe is constructed as a three-way pipe that is connected to the air pump, the valve body and the first pipe respectively, wherein the valve body is configured to control the communication between the air pipe and the outside.

In one possible design, the flowing channel unit includes a three-way valve, a breast flange and a duckbill valve. The three-way valve is formed thereon with a vent channel, a liquid inlet and a liquid outlet respectively. The three-way valve has the breast flange fixed thereon and is communicated with the breast flange through the vent channel. The breast flange is detachably connected to the variable pressure chamber. The liquid outlet of the three-way valve is provided with the duckbill valve. The liquid inlet of the three-way valve is communicated with the outside.

In one possible design, the cup includes a cup body and a silicone trumpet cover.

The cup body has a first opening and a second opening. The first opening is configured to connect to the host machine, and the second opening is provided with the silicone trumpet cover. The silicone trumpet cover has opposite large-diameter end and smaller-diameter end. The large-diameter end is connected to the second opening. The smaller-diameter end extends toward an inside of the cup body and is connected to the flowing channel unit.

Correspondingly, the flowing channel unit is positioned inside the cup body. The flowing channel unit includes a three-way valve and a breast flange. A liquid inlet of the three-way valve is connected to the smaller-diameter end of the silicone trumpet cover. The three-way valve is provided thereon with the breast flange. The breast flange is fixed on the first opening and connected to the variable pressure chamber.

In one possible design, the cup body is formed thereon with an exhaust and liquid extraction port that is positioned on an upper part of the cup body and is adjacent to the host machine.

The present disclosure has the following beneficial effects.

The detachable breast pump has the flowing channel unit arranged inside the cup, achieving structural optimization, whereby making the structure more concise and the shape more beautiful, as well as increasing the integration level and reducing the occupied space. The host machine is detachably connected to the cup, facilitating convenient demounting and cleaning, reducing the labor of reinstalling after demounting and cleaning, and improving the convenience of usage.

Through the pressure transmission channel, the length of the air path is increased, prolonging the path of the infiltrated milk flowing into the host machine and reducing the probability of the milk polluting the host machine. Meanwhile, the pressure transmission channel is conducive to accurately transmitting a negative pressure to the variable pressure chamber, improving the milking effect of the detachable breast pump.

DETAILED DESCRIPTION OF THE EMBODIMENTS

Figure 1:
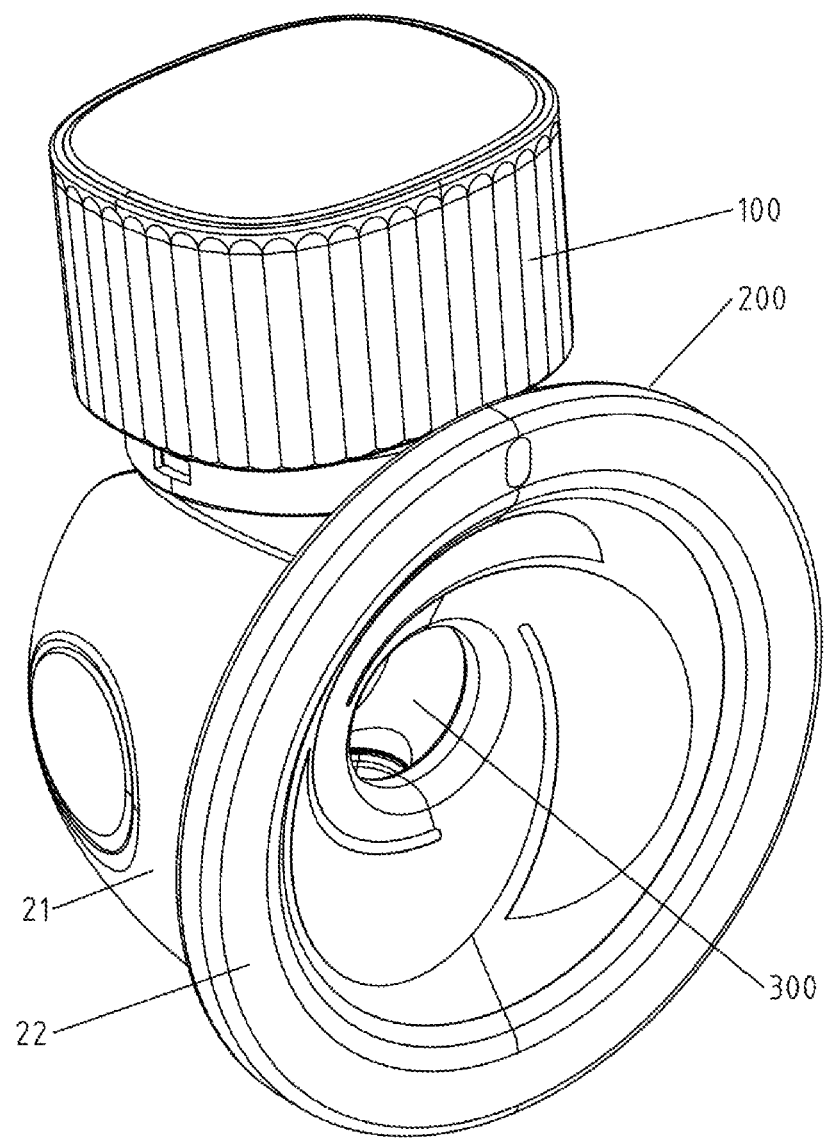
FIG. 1 is a structure diagram of a detachable breast pump.
Figure 2:
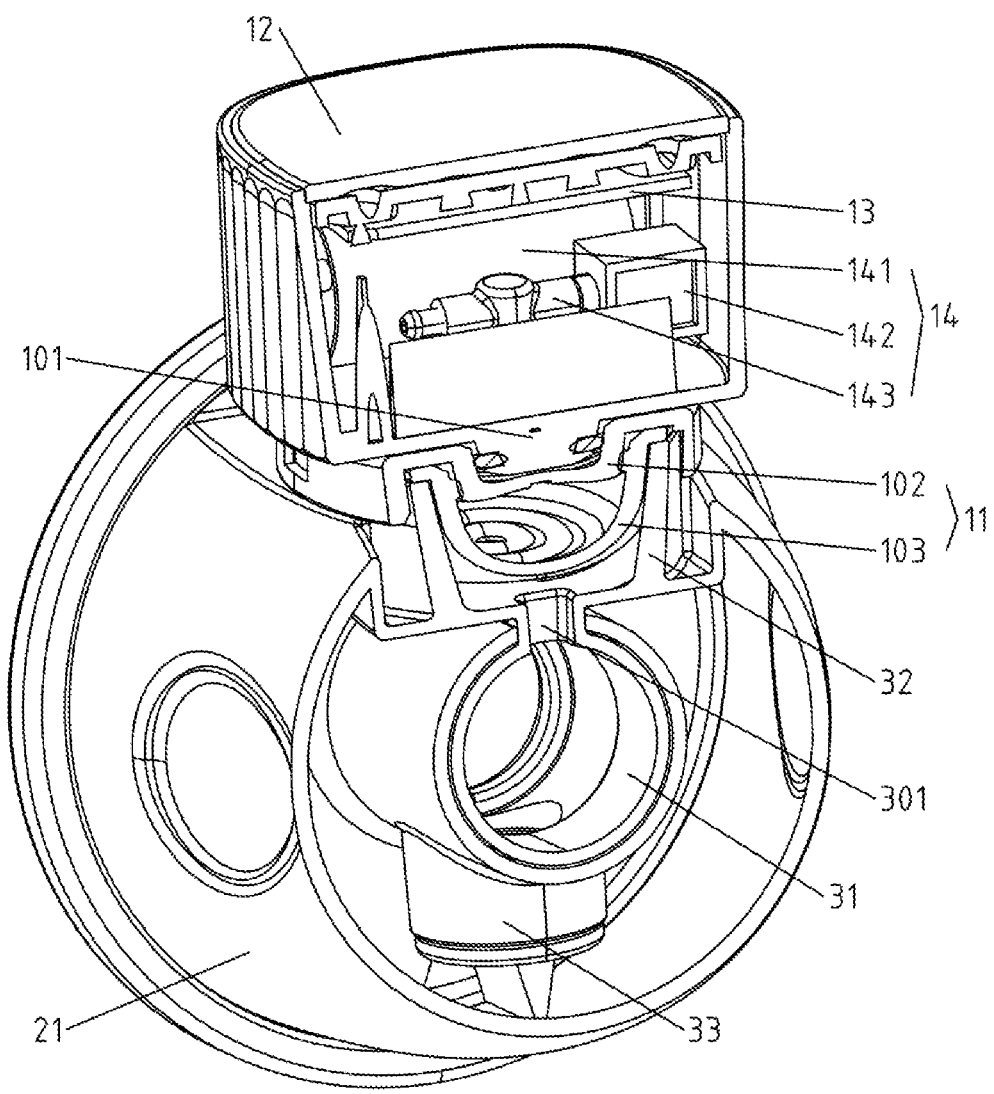
FIG. 2 is a sectional structure diagram of FIG. 1 along a first direction.

For a better understanding of the technical solution in the embodiments of the present disclosure or in the prior art, the present disclosure will be briefly introduced below in combination with the drawings and embodiments or the description of the prior art. Apparently, the descriptions on the drawings of structures below are merely some embodiments of the present disclosure. For the ordinary skill in the field, other drawings may be obtained according to these drawings without creative effort. It should be noted here that the description of these embodiments is merely to help understand the present disclosure, rather than to limit the present disclosure.

Embodiments

As shown in FIG. 1 to FIG. 6, a detachable breast pump includes a host machine 100, a cup 200 and a flowing channel unit 300.

The host machine 100 includes a variable pressure chamber 11. The cup 200 is detachably connected to the host machine 100 through the variable pressure chamber 11. The variable pressure chamber 11 is provided thereon with a pressure transmission channel 400 extended to an inside of the host machine 100.

The flowing channel unit 300 is detachably arranged inside the cup 200 and separates an internal space of the cup 200 into a flowing channel and a milk storage bowl. The flowing channel is communicated with the variable pressure chamber 11, the milk storage bowl and the outside.

Herein, when in use, the detachable breast pump simulates a sucking action to stimulate a breast and initiates milk let-down, allowing the milk stored in breast acini to release through lactiferous ducts. For the released milk, the detachable breast pump simulates the sucking action and generates a negative pressure by which the milk is sucked into the flowing channel and finally stored in the milk storage bowl.

In the above process, the host machine 100 drives the variable pressure chamber 11 to form a negative pressure-positive pressure-negative pressure cycle. The change of pressure is transmitted to a human breast through the flowing channel and the cup 200, simulating the sucking action and stimulating the breast. For the milk flowing into the flowing channel, the positive pressure is recovered and the milk is driven into the milk storage bowl from the flowing channel. The cup 200 on one hand is configured to store the milk, and on the other hand can cover the breast. Through the breast, the flowing channel unit 300 is sealed, forming a relatively enclosed space, whereby to improve the efficiency of milking of the host machine 100. Meanwhile, the cup 200 also guides the milk into the flowing channel unit 300 to flow along the flowing channel.

The flowing channel unit 300 is hidden inside the cup 200, relatively reducing the volume of the milk storage bowl, but then making the structure more concise and the shape more beautiful, as well as increasing the integration level and reducing the occupied space. In addition, through the pressure transmission channel 400, the length of the air path is increased, prolonging the path of the infiltrated milk flowing into the host machine 100 and reducing the probability of the milk polluting the host machine 100. Meanwhile, the pressure transmission channel 400 is conducive to accurately transmitting a negative pressure to the variable pressure chamber, improving the milking effect of the detachable breast pump.

During work, the cup 200 covers a breast, the host machine 100 is started, and the variable pressure chamber 11 forms a negative pressure-positive pressure-negative pressure cycle. The cup 200 combines with the pressure circulation to simulate a sucking action, initiating milk let-down and enabling the milk to flow out. When the variable pressure chamber 11 is at a negative pressure, a sucking force is generated, and the milk is sucked out to flow into the flowing channel. When the variable pressure chamber 11 is at a positive pressure, a push force is generated to push the milk, whereby the milk storage bowl is opened to store the milk. The cycle is repeated, until the milk is completely sucked out. Then, the host machine 100 is shut down, and the detachable breast pump is removed off to flush.

The variable pressure chamber 11 includes a silicone suction cup 103 and forms a negative pressure-positive pressure-negative pressure cycle through the deformation of the silicone suction cup 103. The silicone suction cup 103 is positioned between the host machine 100 and the cup 200, which can block most of the milk entering the host machine 100. However, there is a gap at the connection site of the silicone suction cup 103, and partial milk can pass through the silicone suction cup 103 through the gap and then enters the host machine 100 via the variable pressure chamber 11. Based on the above structure, if there is milk infiltrated into the variable pressure chamber 11, the milk will enter the pressure transmission channel 400 when at a negative pressure and be pushed back into the variable pressure chamber 11 when at a positive pressure. Therefore, the overflowing milk is received in the pressure transmission channel 400, and there is no need to worry that the milk might flow into the host machine 100, whereby to ensure the normal operation of each part inside the host machine 100 and reduce the rate of fault.

Compared with the existing technologies, the detachable breast pump has the flowing channel unit 300 arranged inside the cup 200, achieving structural optimization, whereby making the structure more concise and the shape more beautiful, as well as increasing the integration level and reducing the occupied space. The host machine 100 is detachably connected to the cup 200, facilitating convenient demounting and cleaning, reducing the labor of reinstalling after demounting and cleaning, and improving the convenience of usage.

In the present embodiment, the host machine 100 includes a housing 12, a control module 13 and an air pump module 14. The housing 12 is provided with a partition plate 101 at one end and is connected to the variable pressure chamber 11 through the partition plate 101. The partition plate 101 is provided thereon with a first pipe 401 configured to communicate with the variable pressure chamber 11.

The control module 13 and the air pump module 14 are both arranged inside the housing 12. The control module 13 is connected to the air pump module 14 in a communication manner. The air pump module 14 is connected to the variable pressure chamber 11 through the first pipe 401.

Based on the above design scheme, the housing 12 can be constructed as any appropriate shape, to meet the requirements of different users. The control module 13 on one hand receives a command from a user, and on the other hand transmits the command to the air pump module 14, so that the air pump module 14 generates a corresponding action. It is easy to understand that the control module 13 is inbuilt with multiple work modes, including, but not limited to, a massage mode and a milking mode, and meanwhile can control respective frequencies of the massage mode and the milking mode. The work mode and the work frequency combine with each other to form diverse work states, to meet the requirements of users. The air pump module 14 combines with the variable pressure chamber 11 to form the pressure cycle.

For the variable pressure chamber 11, in order to improve the working effect of the pressure cycle, it is necessary to improve the tightness. Since the flowing channel is communicated with the variable pressure chamber 11, the milk storage bowl and the outside, sealing the first pipe 401 by means of the variable pressure chamber 11 not only improves the tightness, but also reduces the probability that the milk flows into the housing 12 to impact the operation of each part inside the housing 12. Meanwhile, when the detachable breast pump is in use, the cup 200 covers the breast and seals the breast off the outside, whereby the flowing channel is intercommunicated with the milk storage bowl only, ensuring the milk to flow into the milk storage bowl.

The control module 13 can select any appropriate model available on the market. Meanwhile, the control module 13 can be connected to a terminal in a communication manner, so that a user controls the operation of the detachable breast pump through the terminal. Alternatively, the control module 13 further includes a plurality of control buttons arranged outside of the housing 12, so that a user controls the operation of the detachable breast pump through the control buttons.

Optionally, inside the housing 12 is provided a power supply module that is electrically connected to the control module 13 and the air pump module 14 and supplies power to the control module 13 and the air pump module 14. In consideration of the sealed structure of the housing 12, the power supply module preferably selects a rechargeable battery. Correspondingly, the housing 12 is formed thereon with a charging interface electrically connected to the power supply module.

In the present embodiment, the variable pressure chamber 11 includes a spacer 102 and a silicone suction cup 103.

The spacer 102 is detachably connected to the partition plate 101 and is provided thereon with a second pipe 402.

The silicone suction cup 103 includes an annular connection part 104 and a suction cup body 105. The annular connection part 104 has an upper end connected to the spacer 102 and a lower end integrated with the suction cup body 105. The suction cup body 105 is arranged opposite to the spacer 102 to enclose a variable pressure chamber body.

Correspondingly, the second pipe 402 has an upper end communicated with the first pipe 401 and a lower end communicated with the variable pressure chamber body. The first pipe 401 and the second pipe 402 constitute the pressure transmission channel 400.

Based on the above design scheme, a cavity is formed between the spacer 102 and the suction cup body 105, that is, the variable pressure chamber body. In addition, the spacer 102 is provided thereon with the second pipe 402 that is communicated with the air pump module 14 through the first pipe 401. The air pump module 14 sends air into and out of an inside of the variable pressure chamber body, whereby driving the suction cup body 105 to reciprocate. The activity of the suction cup body 105 causes respective changes of volume of the variable pressure chamber body and the flowing channel, finally achieving the effect of the pressure cycle. In addition, the application of the silicone suction cup 103 enables a more uniform change of pressure inside the flowing channel, not only improving the working effect of the detachable breast pump, but also being conducive to protecting the breast.

When the detachable breast pump needs to be cleaned after usage, the host machine 100 is detached from the cover 200, so that the variable pressure chamber 11 is exposed. That is, the silicone suction cup 103 is exposed, so only the suction cup body 105 is to be washed, which effectively improves the cleaning effect and avoids milk residue. It is easy to understand that for the silicone suction cup 103, at least the suction cup body 105 is made of silicone, which facilitates the reciprocation with pressure changes.

Figure 5:
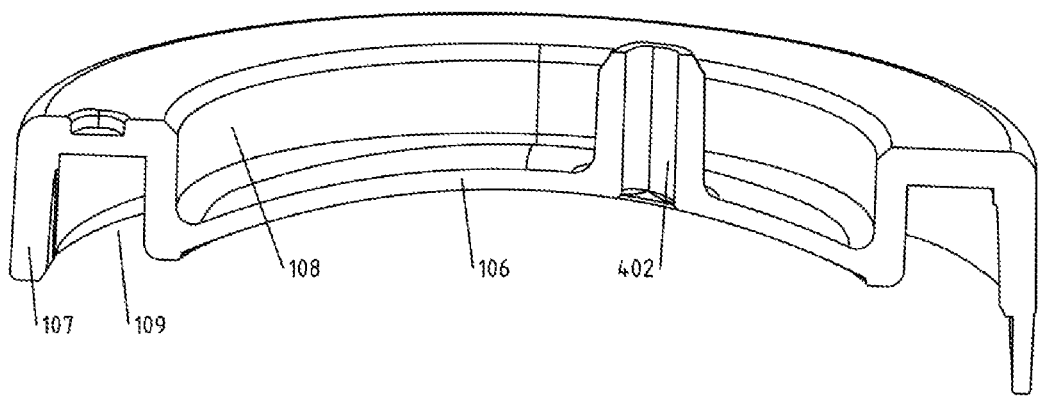
FIG. 5 is a structure diagram of a spacer.

As shown in FIG. 5, the spacer 102 includes a spacer body 106 and a peripheral connection part 107. The spacer body 106 is arranged opposite to the partition plate 101. An outer circumference of the spacer body 106 is connected to the peripheral connection part 107. The peripheral connection part 107 includes an inner annular surface 108 and a clamping groove 109 with a downward opening. The inner annular surface 108 is clamped to the partition plate 101 through a snap ring. The clamping groove 109 is configured to connect to the annular connection part 104. Correspondingly, the partition plate 101 has a bottom surface provided thereon with an annular plate 110 fitting with the inner annular surface 108.

Based on the above design scheme, the milk infiltrated via the flowing channel can only pass through the silicone suction cup 103 through the clamping groove 109 to flow into the variable pressure chamber body, which greatly increases the difficulty of the milk infiltrating into the host machine 100 and hence protects the host machine 100.

Figure 3:
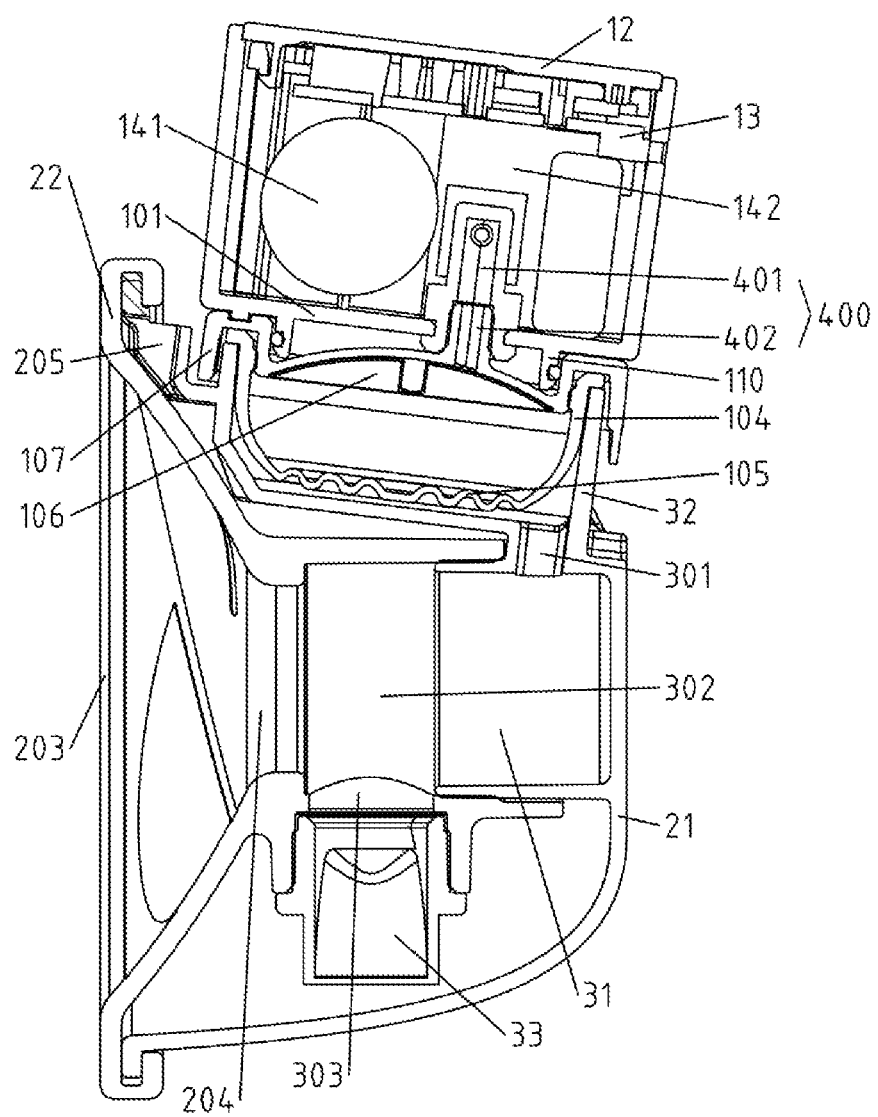
FIG. 3 is a sectional structure diagram of FIG. 1 along a second direction.
Figure 4:
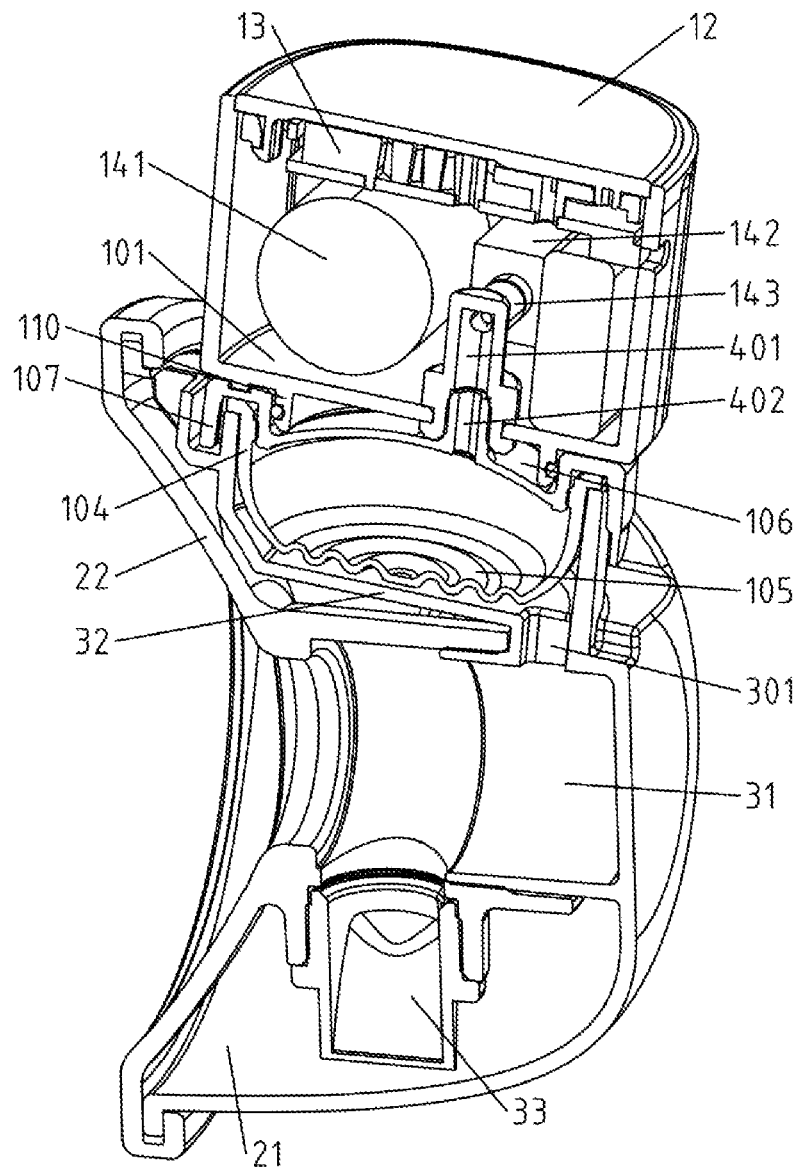
FIG. 4 is an isometric structure diagram of FIG. 3.

As shown in FIG. 3 and FIG. 4, the connection between the spacer body 106 and the partition plate 101 is detachable connection, where up-down plugging and unplugging can enable demounting. The connection between the annular connection part 104 and the clamping groove 109 is detachable connection as well, where up-down plugging and unplugging can enable demounting. As a result, the demounting ability is improved, which is helpful to achieve thorough cleaning and reduce milk residue.

In the present embodiment, the air pump module 14 includes an air pump 141, a valve body 142 and an air pipe 143. The air pump 141 and the valve body 142 are each connected to the control module 13 in a communication manner. The air pipe 143 is constructed as a three-way pipe that is connected to the air pump 141, the valve body 142 and the first pipe 401 respectively, wherein the valve body 142 is configured to control the communication between the air pipe 143 and the outside.

Based on the above design scheme, the air pump 141 is communicated with the variable pressure chamber body through the air pipe 143, that is, the air pipe 143 is communicated with the variable pressure chamber body through the pressure transmission channel 400. The air pump 141 sucks in air after being started, whereby to cause the suction cup body 105 to move upwardly and form a negative pressure. The silicone suction cup 103 moves to an upper limit position, the valve body 142 is turned on, and external air enters the air pipe 143 and flows into the variable pressure chamber body via the pressure transmission channel 400, forming a positive pressure and driving the suction cup body 105 to move downwardly. The silicone suction cup 103 moves to a lower limit position, then the valve body 142 is turned off, and the air pump 141 sucks in air again, achieving a reciprocation of the suction cup body 105, hence achieving the pressure cycle.

It is understandable that the air pump 141 is connected to the control module 13 in a communication manner, and the air pump 141 can select any model available on the market. The valve body 142 preferably selects a solenoid valve, and the solenoid valve is connected to the control module 13 in a communication manner. The air pipe 143 selects any appropriate model available on the market.

In the present embodiment, the flowing channel unit 300 includes a three-way valve 31, a breast flange 32 and a duckbill valve 33. The three-way valve 31 is formed thereon with a vent channel 301, a liquid inlet 302 and a liquid outlet 303 respectively. The three-way valve 31 has the breast flange 32 fixed thereon and is communicated with the breast flange 32 through the vent channel 301. The breast flange 32 is detachably connected to the variable pressure chamber 11. The liquid outlet 303 of the three-way valve 31 is provided with the duckbill valve 33. The liquid inlet 302 of the three-way valve 31 is communicated with the outside.

Based on the above design scheme, the three-way valve 31 is connected to the variable pressure chamber 11 through the breast flange 32, and the breast flange 32 is detachably connected to the variable pressure chamber 11, so that it can be detached to flush after milking. Meanwhile, a cavity is formed between the breast flange 32 and the variable pressure chamber 11, and the cavity is communicated with the three-way valve 31 through the vent channel 301. The variable pressure chamber 11, the cavity, the vent channel 301 and the three-way valve 31 form an intercommunicated air path, then the change of pressure inside the variable pressure chamber 11 will be transmitted to the three-way valve 31. The duckbill valve 33 is one type of one-way valve, that is, when the milk is pushed by a positive pressure, the duckbill valve 33 is turned on, so that the milk flows into the milk storage bowl from the flowing channel. The duckbill valve 33 is turned off at a negative pressure or normal pressure, preventing the milk inside the milk storage bowl from flowing out, hence reducing the possibility of leakage of milk.

Figure 6:
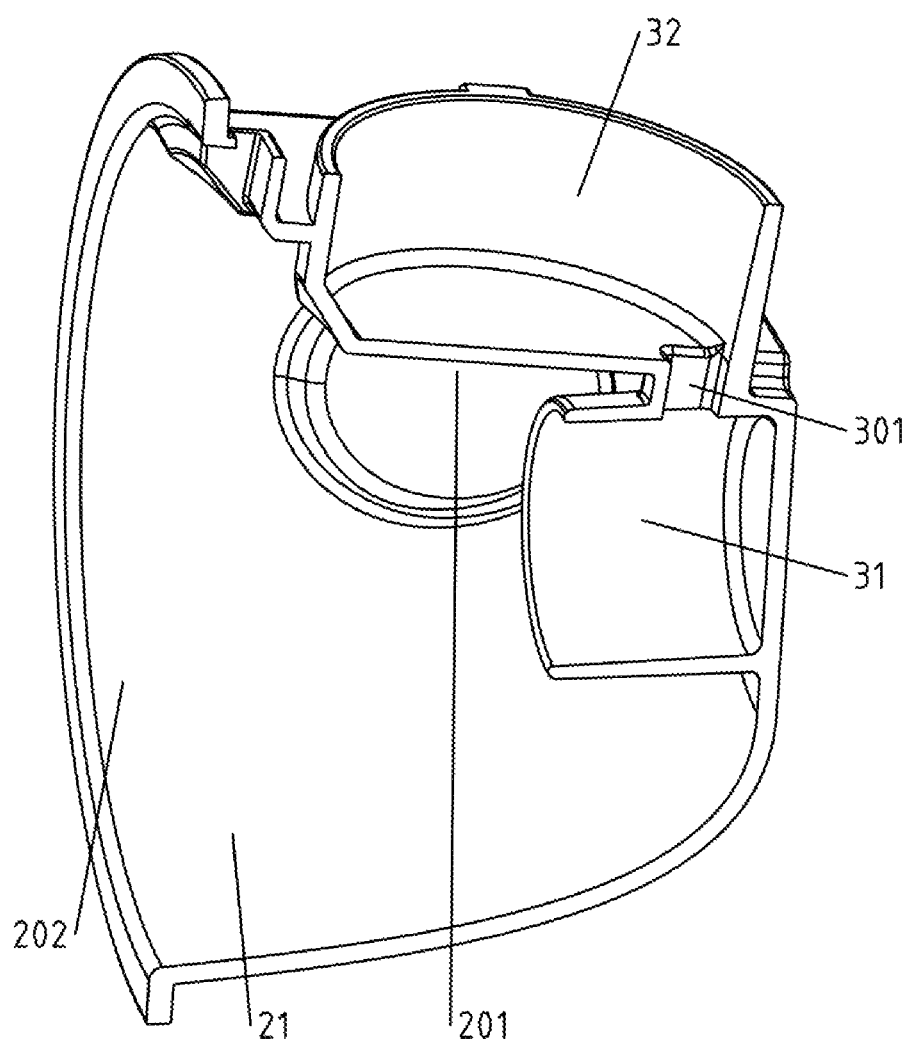
FIG. 6 is a structure diagram of a cup body.
In the drawings:
100, a host machine; 11, a variable pressure chamber; 12, a housing; 13, a control module; 14, an air pump module; 101, a partition plate; 102, a spacer; 103, a silicone suction cup; 104, an annular connection part; 105, a suction cup body; 106, a spacer body; 107, a peripheral connection part; 108, an inner annular surface; 109, a clamping groove; 110, an annular plate; 141, an air pump; 142, a valve body; 143, an air pipe; 200, a cup; 21, a cup body; 22, a silicone trumpet cover; 201, a first opening; 202, a second opening; 203, a large-diameter end; 204, a smaller-diameter end; 205, an exhaust and liquid extraction port; 300, a flowing channel unit; 31, a three-way valve; 32, a breast flange; 33, a duckbill valve; 301, a vent channel; 302, a liquid inlet; 303, a liquid outlet; 400, a pressure transmission channel; 401, a first pipe; and 402, a second pipe.

Optionally, as shown in FIG. 6, an outer circumference of the breast flange 32 is connected to the cup 200, preferably, the breast flange 32 is integrally formed with the cup 200. A top of the breast flange 32 presents an annular shape and can be inserted into the clamping groove 109, that is, the annular connection part 104 and the breast flange 32 are inserted into the clamping groove 109 at the same time, achieving the connection between the flowing channel unit 300 and the variable pressure chamber 11. Herein, the connection is detachable connection as well, where up-down plugging and unplugging can enable demounting, making subsequent cleaning convenient.

In the present embodiment, the cup 200 includes a cup body 21 and a silicone trumpet cover 22.

The cup body 21 has a first opening 201 and a second opening 202. The first opening 201 is configured to connect to the host machine 100, and the second opening 202 is provided with the silicone trumpet cover 22. The silicone trumpet cover 22 has opposite large-diameter end 203 and smaller-diameter end 204. The large-diameter end 203 is connected to the second opening 202. The smaller-diameter end 204 extends toward an inside of the cup body 21 and is connected to the flowing channel unit 300.

Correspondingly, the flowing channel unit 300 is positioned inside the cup body 21. The flowing channel unit 300 includes a three-way valve 31 and a breast flange 32. A liquid inlet 302 of the three-way valve 31 is connected to the smaller-diameter end 204 of the silicone trumpet cover 22. The three-way valve 31 is provided thereon with the breast flange 32; and the breast flange 32 is fixed on the first opening 201 and connected to the variable pressure chamber 11.

Based on the above design scheme, the cup body 21 can be constructed as any appropriate shape, as long as a certain space can be enclosed. The variable pressure chamber 11 is fixed on the first opening 201. Specifically, the cup body 21 is connected to the variable pressure chamber 11 through the breast flange 32, and the silicone trumpet cover 22 is clamped onto the second opening 202. Meanwhile, the flowing channel unit 300 is positioned inside the cup body 21. Therefore, the flowing channel unit 300 should be placed inside the cup body 21 before the silicone trumpet cover 22 is clamped onto the cup body 21. The flowing channel unit 300 is connected to the variable pressure chamber 11 to achieve preliminary fixation. In view of the above, the variable pressure chamber 11 and the silicone trumpet cover 22 can achieve a sealing effect to isolate the milk storage bowl from the outside.

An outer circumferential surface of the silicone trumpet cover 22 is covered inside the cup body 21 to seal the cup body 21. An inner circumferential surface of the silicone trumpet cover 22 is constructed as a curved surface fitting with the curve of the breast, achieving a better fitness to improve the stimulating effect on the breast. Meanwhile, the silicone trumpet cover 22 selects silicone having certain elasticity, which can stimulate or massage the breast under the action of the pressure cycle. Therefore, besides the milking function, the detachable breast pump can also be used for massaging the breast, achieving function expansion.

Optionally, as shown in FIG. 3, the three-way valve 31 has two opposite ends. One end is embedded on the cup body 21 while the other end is clamped to the silicone trumpet cover 22. Alternatively, one end of the three-way valve 31 is directly opposite to an inner wall of the cup body 21 while the other end is clamped to the silicone trumpet cover 22.

In one possible implementation, the cup body 21 is formed thereon with an exhaust and liquid extraction port 205 that is positioned on an upper part of the cup body 21 and is adjacent to the host machine 100. Based on the above design scheme, when the milk flows into the milk storage bowl, the air inside the milk storage bowl is exhausted through the exhaust and liquid extraction port 205, ensuring the milk to successfully flow into the milk storage bowl. The milk stored in the milk storage bowl can also be poured out through the exhaust and liquid extraction port 205, for subsequent usage. Meanwhile, the exhaust and liquid extraction port 205 is positioned on the upper part of the cup body 21 and is adjacent to the host machine 100. Relatively, the exhaust and liquid extraction port 205 is positioned above, whereby reducing the risk of leakage of milk.

Finally, it should be noted that the above are preferred embodiments of the present disclosure merely and are not intended to limit scope of protection of the present disclosure. Any modifications, equivalent substitutions and improvements, etc., made within the spirit and principle of the present disclosure are all intended to be included in the scope of protection of the present disclosure.

What is claimed is:

1. A detachable breast pump, comprising a host machine (100), a cup (200) and a flowing channel unit (300);
    the host machine (100) comprising a variable pressure chamber (11), the cup (200) being detachably connected to the host machine (100) through the variable pressure chamber (11), and the variable pressure chamber (11) being provided thereon with a pressure transmission channel (400) extended to an inside of the host machine (100); and
    the flowing channel unit (300) being detachably arranged inside the cup (200) and separating an internal space of the cup (200) into a flowing channel and a milk storage bowl, and the flowing channel being communicated with the variable pressure chamber (11), the milk storage bowl and the outside;
    wherein the host machine (100) comprises a housing (12), a control module (13) and an air pump module (14); the housing (12) is provided with a partition plate (101) at one end and is connected to the variable pressure chamber (11) through the partition plate (101); and the partition plate (101) is provided thereon with a first pipe (401) configured to communicate with the variable pressure chamber (11); and
    the control module (13) and the air pump module (14) are both arranged inside the housing (12); the control module (13) is connected to the air pump module (14) in a communication manner; and the air pump module (14) is connected to the variable pressure chamber (11) through the first pipe (401);
    wherein the air pump module (14) comprises an air pump (141), a valve body (142) and an air pipe (143); the air pump (141) and the valve body (142) are each connected to the control module (13) in a communication manner; the air pipe (143) is constructed as a three-way pipe that is connected to the air pump (141), the valve body (142) and the first pipe (401) respectively, wherein the valve body (142) is configured to control the communication between the air pipe (143) and the outside.

2. The detachable breast pump according to claim 1, wherein the variable pressure chamber (11) comprises a spacer (102) and a silicone suction cup (103);
    the spacer (102) is detachably connected to the partition plate (101) and is provided thereon with a second pipe (402);
    the silicone suction cup (103) comprises an annular connection part (104) and a suction cup body (105); the annular connection part (104) has an upper end connected to the spacer (102) and a lower end connected to the suction cup body (105); the suction cup body (105) is arranged opposite to the spacer (102) to enclose a variable pressure chamber body; and
    correspondingly, the second pipe (402) has an upper end communicated with the first pipe (401) and a lower end communicated with the variable pressure chamber body; and the first pipe (401) and the second pipe (402) constitute the pressure transmission channel (400).

3. The detachable breast pump according to claim 2, wherein the spacer (102) comprises a spacer body (106) and a peripheral connection part (107); the spacer body (106) is arranged opposite to the partition plate (101); an outer circumference of the spacer body (106) is connected to the peripheral connection part (107); the peripheral connection part (107) comprises an inner annular surface (108) and a clamping groove (109) with a downward opening; the inner annular surface (108) is clamped to the partition plate (101) through a snap ring; the clamping groove (109) is configured to connect to the annular connection part (104); and correspondingly, the partition plate (101) has a bottom surface provided thereon with an annular plate (110) fitting with the inner annular surface (108).

4. The detachable breast pump according to claim 1, wherein the flowing channel unit (300) comprises a three-way valve (31), a breast flange (32) and a duckbill valve (33); the three-way valve (31) is formed thereon with a vent channel (301), a liquid inlet (302) and a liquid outlet (303) respectively; the three-way valve (31) has the breast flange (32) fixed thereon and is communicated with the breast flange (32) through the vent channel (301); the breast flange (32) is detachably connected to the variable pressure chamber (11); the liquid outlet (303) of the three-way valve (31) is provided with the duckbill valve (33); and the liquid inlet (302) of the three-way valve (31) is communicated with the outside.

5. The detachable breast pump according to claim 4, wherein the cup (200) comprises a cup body (21) and a silicone trumpet cover (22);
    the cup body (21) has a first opening (201) and a second opening (202); the first opening (201) is configured to connect to the host machine (100), and the second opening (202) is provided with the silicone trumpet cover (22); the silicone trumpet cover (22) has opposite large-diameter end (203) and smaller-diameter end (204); the large-diameter end (203) is connected to the second opening (202); and the smaller-diameter end (204) extends toward an inside of the cup body (21) and is connected to the flowing channel unit (300); and
    correspondingly, the flowing channel unit (300) is positioned inside the cup body (21); the flowing channel unit (300) comprises a three-way valve (31) and a breast flange (32); a liquid inlet of the three-way valve (31) is connected to the smaller-diameter end (204) of the silicone trumpet cover (22); the three-way valve (31) is provided thereon with the breast flange (32); and the breast flange (32) is fixed on the first opening (201) and connected to the variable pressure chamber (11).

6. The detachable breast pump according to claim 5, wherein the cup body (21) is formed thereon with an exhaust and liquid extraction port (205) that is positioned on an upper part of the cup body (21) and is adjacent to the host machine (100).

* * * * *